(12) United States Patent
Case et al.

(10) Patent No.: US 10,096,148 B1
(45) Date of Patent: Oct. 9, 2018

(54) PORTABLE X-RAY COMPUTED TOMOGRAPHY

(71) Applicant: The Aerospace Corporation, El Segundo, CA (US)

(72) Inventors: Joseph T. Case, El Segundo, CA (US); Shant Kenderian, El Segundo, CA (US); Eric C. Johnson, El Segundo, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 15/497,280

(22) Filed: Apr. 26, 2017

(51) Int. Cl.
  *G06T 15/08* (2011.01)
  *G01N 23/046* (2018.01)
  *G06T 11/00* (2006.01)

(52) U.S. Cl.
  CPC .......... *G06T 15/08* (2013.01); *G01N 23/046* (2013.01); *G06T 11/006* (2013.01); *G06T 11/008* (2013.01); *G01N 2223/401* (2013.01); *G01N 2223/419* (2013.01); *G06T 2207/10081* (2013.01); *G06T 2211/424* (2013.01)

(58) Field of Classification Search
  USPC ................................................ 382/128, 131
  See application file for complete search history.

(56) References Cited

U.S. PATENT DOCUMENTS

| | | | |
|---|---|---|---|
| 6,002,739 A * | 12/1999 | Heumann | ............ G06T 11/006 378/21 |
| 6,765,981 B2 | 7/2004 | Heumann | |
| 6,973,157 B2 | 12/2005 | Claus | |
| 7,916,828 B1 * | 3/2011 | Khare | .................... A61B 6/466 378/4 |
| 9,057,680 B2 | 6/2015 | Jung et al. | |
| 9,129,425 B2 | 9/2015 | Myers et al. | |
| 9,194,828 B2 | 11/2015 | Turner | |
| 9,230,323 B2 | 1/2016 | Kobayashi et al. | |
| 9,373,159 B2 | 6/2016 | Amroabadi et al. | |

(Continued)

OTHER PUBLICATIONS

A. C. Kak and Malcolm Slaney, Principles of Computerized Tomographic Imaging, Ch. 7, pp. 275-96, https://engineering.purdue.edu/~malcolm/pct/CTI_Ch07.pdf, IEEE Press (1988).

(Continued)

*Primary Examiner* — Ishrat I Sherali
(74) *Attorney, Agent, or Firm* — LeonardPatel PC

(57) ABSTRACT

A portable x-ray computed tomography (CT) system may utilize algebraic reconstruction techniques (ART) to produce 3D volume images from tens of shots or less. The system may be deployed as desired where x-ray source and detector positions are not known beforehand. A fast, accurate matrix may be formed relating voxels to detector pixels via a modified ray tracing algorithm, eliminating artifacts caused by approaches using rough approximations. Masking or recombination may be performed to remove detector pixels that are not part of a region of interest (ROI) or lump the pixels together as one unknown, significantly reducing matrix size, and hence, computation time. The positions and orientations of the x-ray source and detector may be treated as unknowns and refined to optimize a volume image metric. For example, the optimized metric could be image contrast, image sparsity, or total variation.

20 Claims, 8 Drawing Sheets

(56) References Cited

U.S. PATENT DOCUMENTS

| | | | |
|---|---|---|---|
| 9,875,558 B2* | 1/2018 | Yang | G06T 11/003 |
| 2008/0058611 A1 | 3/2008 | Tsubura | |
| 2009/0290772 A1 | 11/2009 | Avinash et al. | |
| 2012/0140876 A1 | 6/2012 | Jung et al. | |
| 2013/0243151 A1 | 9/2013 | Shih | |
| 2013/0315368 A1 | 11/2013 | Turner | |
| 2013/0315369 A1 | 11/2013 | Turner | |
| 2013/0336562 A1* | 12/2013 | Zamyatin | G06T 11/006 382/131 |
| 2013/0343629 A1 | 12/2013 | Myers et al. | |
| 2015/0125059 A1* | 5/2015 | Holmes | A61B 6/032 382/131 |
| 2015/0187052 A1 | 7/2015 | Amroabadi et al. | |
| 2015/0332455 A1 | 11/2015 | Kobayashi et al. | |
| 2015/0377803 A1 | 12/2015 | Turner | |
| 2016/0034598 A1 | 2/2016 | Baranov et al. | |
| 2016/0063694 A1 | 3/2016 | Shi | |
| 2016/0135779 A1 | 5/2016 | Kim et al. | |
| 2016/0143609 A1 | 5/2016 | Park et al. | |
| 2016/0224229 A1 | 8/2016 | Jo et al. | |
| 2016/0247302 A1 | 8/2016 | Pan et al. | |
| 2016/0256128 A1 | 9/2016 | Wang et al. | |
| 2016/0317107 A1 | 11/2016 | Zhou et al. | |
| 2016/0345924 A1 | 12/2016 | Foos et al. | |
| 2016/0358740 A1 | 12/2016 | Hu | |

OTHER PUBLICATIONS

Fu et al., Abstract only of "Analysis and Accurate Reconstruction of incomplete Data in X-Ray Differential Phase-Contrast Computed Tomography" (remainder of article was not accessible without subscription), http://link.springer.com/article/10.1007/s00216-013-7482-0 (last accessed Dec. 15, 2017).

Wikipedia Algebraic Reconstruction Technique Article, https://en.wikipedia.org/wiki/Algebraic_Reconstruction_Technique (last accessed Dec. 15, 2016).

* cited by examiner

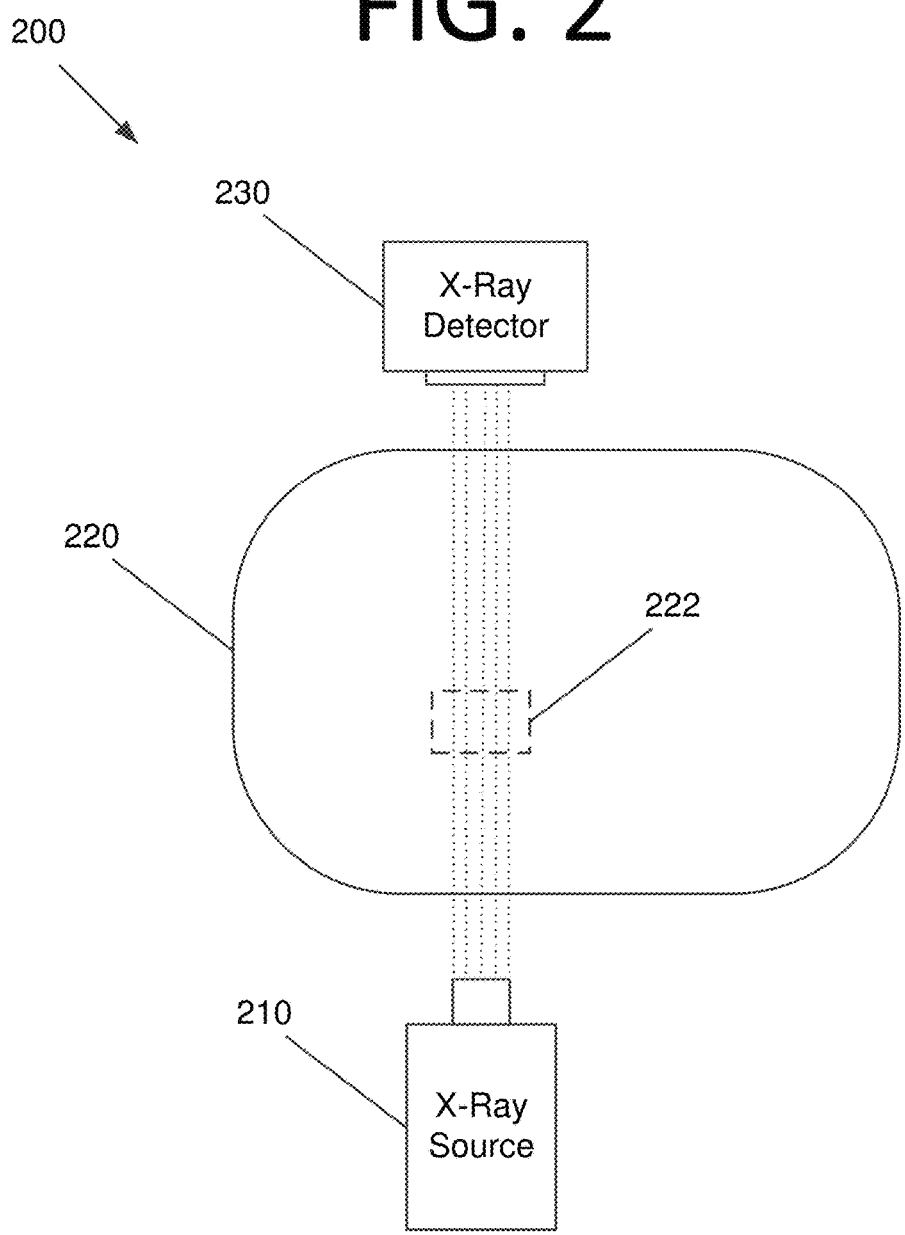

300

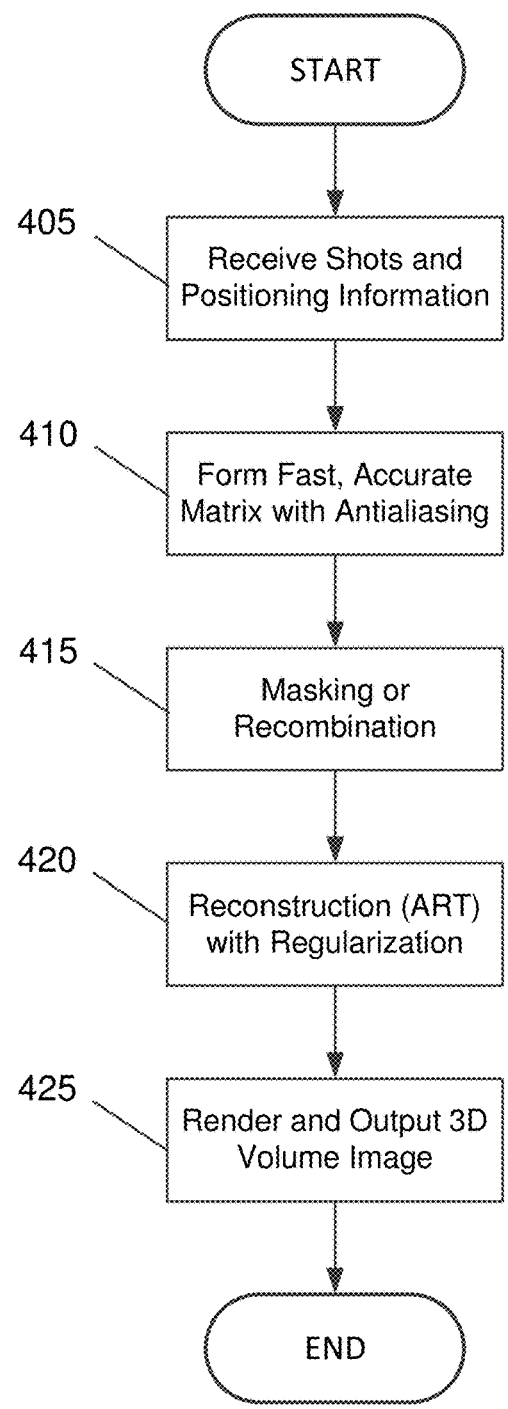

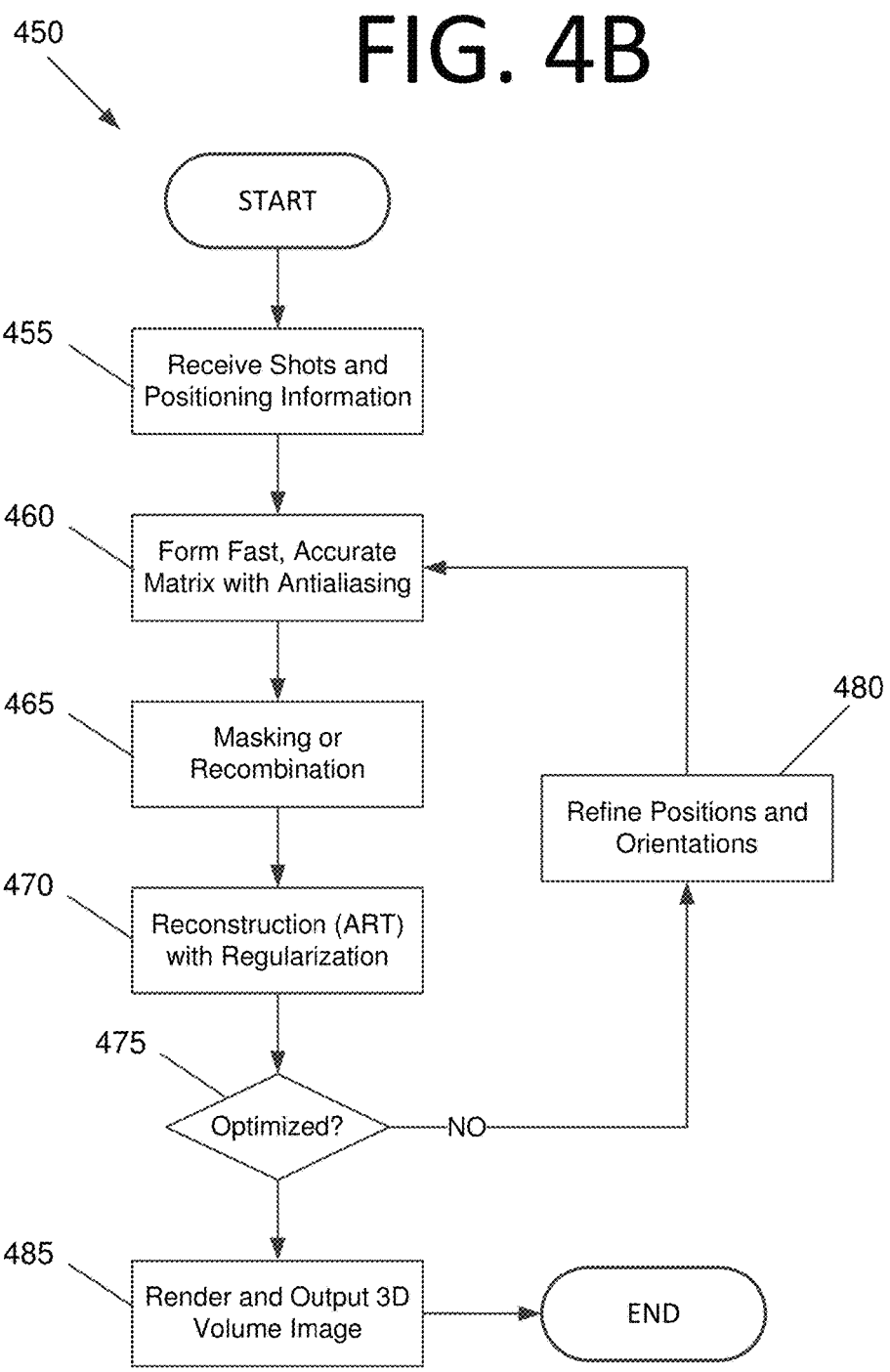

PORTABLE X-RAY COMPUTED TOMOGRAPHY

STATEMENT OF GOVERNMENT INTEREST

This invention was made with government support under Contract No. FA8802-14-C-0001 awarded by the Department of the Air Force. The government has certain rights in the invention.

FIELD

The present invention generally pertains to x-ray computed tomography, and more particularly, to portable x-ray computed tomography (CT) that utilizes algebraic reconstruction techniques (ART).

BACKGROUND

X-ray CT is the de facto standard for volumetric inspection. Parts, or any other object, person, or animal to be analyzed, are typically placed into a stationary cabinet where the part is rotated between an x-ray source and an x-ray detector. Parts may also be slowly marched through a rotating ring containing an x-ray source and x-ray detector.

Thousands of x-ray shots are taken of the part at unique angles of incidence. A volume image may be formed from these x-ray shots through a process called reconstruction. Conventional commercial reconstruction techniques use processes based on the Radon transform, which is why a large number of x-ray shots are required. The volume image may then be rendered, sliced, or dissected during analysis to measure features or diagnose failures in the part under inspection.

Conventional x-ray CT cannot be used for parts that do not fit within the cabinet or ring. Some x-ray systems exist that are advertised as "portable." However, they are heavy, dedicated systems that require the part under inspection to be manipulated through a ring. While such systems may find some application, they are generally limited and impractical. For parts in the field, it may only be reasonable, or even possible, to capture a limited number of shots at unique angles of incidence compared to the thousands of shots required in a conventional CT scan, and it may be difficult or impossible to exploit rotational symmetry. Also, a large number of unique x-ray shots may not be possible. Accordingly, an improved x-ray process and system may be beneficial.

SUMMARY

Certain embodiments of the present invention may be implemented and provide solutions to the problems and needs in the art that have not yet been fully solved by conventional x-ray CT technologies. For example, some embodiments pertain to portable x-ray CT that utilizes ART.

In an embodiment, a computer-implemented method includes receiving, by a computing system, a plurality of x-ray shots from an x-ray detector and position information from at least one positioning system, the plurality of x-ray shots comprising detector pixels. The computer-implemented method also includes forming a matrix, by the computing system, relating voxels to detector pixels for each of the plurality of x-ray shots. This may be done using a ray tracing algorithm or a similar algorithm, for instance. The matrix may be formed specifically to reduce or eliminate volume image artifacts. The computer-implemented method further includes performing masking or recombination, by the computing system, to remove the detector pixels that are not part of a region of interest (ROI) or lump these detector pixels together as one or more unknowns (e.g., a few unknowns). Additionally, the computer-implemented method includes performing ART-based reconstruction with regularization, by the computing system, to produce a 3D volume image, and rendering and outputting the 3D volume image, by the computing system.

In another embodiment, a computer program is embodied on a non-transitory computer-readable medium. The program is configured to cause at least one processor to form a matrix A relating voxels to detector pixels for each of a plurality of x-ray shots. This may be done using a ray tracing algorithm or a similar algorithm, for instance. The computer program is also configured to cause the at least one processor to perform masking or recombination. The computer program is further configured to cause the at least one processor to perform ART-based reconstruction with regularization to produce a 3D volume image, and render and output the 3D volume image.

In yet another embodiment, a computer-implemented method includes receiving, by a computing system, a plurality of x-ray shots from an x-ray detector and position information from at least one positioning system, the plurality of x-ray shots comprising detector pixels. The computer-implemented method also includes forming a matrix, by the computing system, relating voxels to detector pixels for each of the plurality of x-ray shots and performing masking or recombination, by the computing system, to remove the detector pixels that are not part of a ROI or lump these detector pixels together as one or more unknowns (e.g., a few unknowns). The computer-implemented method further includes performing ART-based reconstruction with regularization, by the computing system, to produce a 3D volume image, and rendering and outputting the 3D volume image, by the computing system.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 2 an architectural diagram illustrating a portable x-ray CT system with an x-ray source and detector positioned around a large target, according to an embodiment of the present invention.

FIG. 4A is a flowchart illustrating a process for performing x-ray CT using ART-based techniques, according to an embodiment of the present invention.

FIG. 4B is a flowchart illustrating another process for performing x-ray CT using ART-based techniques, according to an embodiment of the present invention.

DETAILED DESCRIPTION OF THE EMBODIMENTS

Some embodiments of the present invention pertain to portable x-ray computed tomography that utilizes ART. An advantage of using ART is that it does not require rotational symmetry, does not require many shots, and does not require shots of the entire part. Such embodiments may circumvent the aforementioned challenges of conventional systems for producing high resolution "CT-like" volume images of parts in the field and/or large parts or regions of interest on large parts.

By using ART, some embodiments may perform reconstruction from tens of individual x-ray shots, rather than hundreds or thousands, as required conventionally. Since the accurate positions and orientations of the x-ray source and detector for each x-ray shot may not be known, these may be back-calculated through the optimization of a volume image metric. Despite the limited number of individual shots used, this results in volume images that can be captured in the field with fidelity comparable to that of a conventional CT scan. Shots of an entire part may also not be required, which is useful for inspecting smaller regions of interest of a large part.

Another distinct advantage of some embodiments is that the x-ray source and detector may be moved freely around the part under inspection in a light form factor rather than being constrained to a heavy ring geometry. Such a system may be known as an "arbitrary shot" or a "no ring" system, which does not exist in industry. However, there is no harm in collecting data in a "ring" or "split-ring" configuration for some applications, and some embodiments may use such a design. Also, since the parameters of source and detector positions and orientation should be known exactly with respect to the part, these parameters may be back-calculated by optimizing an image metric of the reconstructed volume image. The end result is a flexible, lightweight, and robust portable x-ray CT system that may be useful for field inspections.

Figure 1:
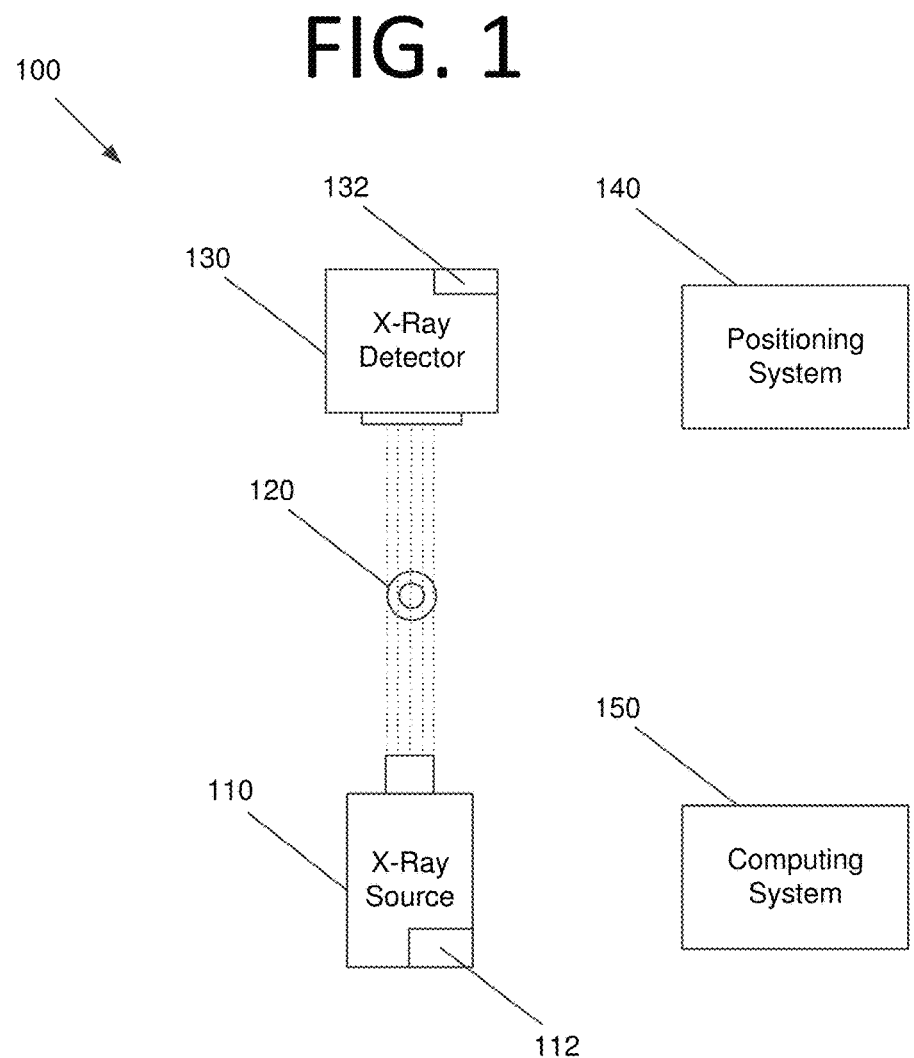
FIG. 1 is an architectural diagram illustrating a portable x-ray CT system, according to an embodiment of the present invention.

The portable x-ray CT system of some embodiments includes an x-ray source, an x-ray detector, a positioning system, and a computing system for reconstruction. Such a system 100 is shown in FIG. 1. System 100 includes an x-ray source 110, a target 120 (here, a nut), an x-ray detector 130, an external positioning system 140, and a computing system 150. In this embodiment, both x-ray source 110 and x-ray detector 130 can determine their positions and orientations using internal positioning systems 112, 132, respectively, such as one or more global positioning systems (GPSs), gyros, accelerometers, laser positioning systems, ultrasonic positioning systems, camera-based positioning systems, markers, string encoders, any combination thereof, or any other suitable location determination and positioning system without deviating from the scope of the invention. The positions and orientations of x-ray source 110 and x-ray detector 130 may be mapped to a common coordinate system and orientation reference, respectively. Positioning systems may be provided either as separate equipment (e.g., positioning system 140) or as hardware and/or software included as part of computing system 150. Including internal positioning systems 112, 132 and an external positioning system 140 may be redundant, and may not be needed in some embodiments.

Alternatively, when an accurate positioning system (and thus, accurate positioning information) is not available, accurate x-ray source 110 and x-ray detector 130 positions and orientations may be determined by including a known target in the region of interest (ROI) when the x-ray shots are made. This known target serves as a reference such that an iterative solver may be used to optimize a cost function representing the difference between an intermediate reconstructed volume image and an ideal reference image. Thus, positions and orientations may be back-calculated from the x-ray shots. In certain embodiments, a known target is not used and instead, a volume image metric may be optimized to provide the same or similar accurate x-ray source 110 and x-ray detector 130 positions. Image metrics may include, but are not limited to, image contrast, sparsity, and total variation.

Computing system 140 may receive x-ray shot data from detector 130 and perform ART processing itself or transmit the x-ray shot data to one or more other computing systems for processing. For instance, if computing system 140 is a portable computing system (e.g., a laptop, tablet, cell phone, etc.), it may transmit the image data to a server, cloud computing system, supercomputer, and/or any other suitable computing system(s) without deviating from the scope of the invention. Such computing systems may be able to perform more complex processing, and may be able to perform processing in real-time or near-real time. Processed volume images may then be transmitted to computing system 140 for a user to view.

FIG. 2 illustrates a portable x-ray CT system 200 with an x-ray source 210 and an x-ray detector 230 positioned around a large target 220. Due to the size of target 220, only a portion of target 220 would be imaged. Here, a ROI, which includes a subcomponent 222 of target 220, is imaged.

The x-ray source and detector in some embodiments may be manipulated automatically or manually to take shots (x-ray images) of the ROI. The location and orientation of the x-ray source and detector should be known for every x-ray shot. This location and orientation may be provided by the positioning system. The x-ray shots, locations, and orientations may then be provided to a computing system to reconstruct the volume image of the ROI using ART-based algorithms. The locations and orientations may then be revised in an iterative reconstruction process through an optimization of a volume image metric.

Figure 3A:
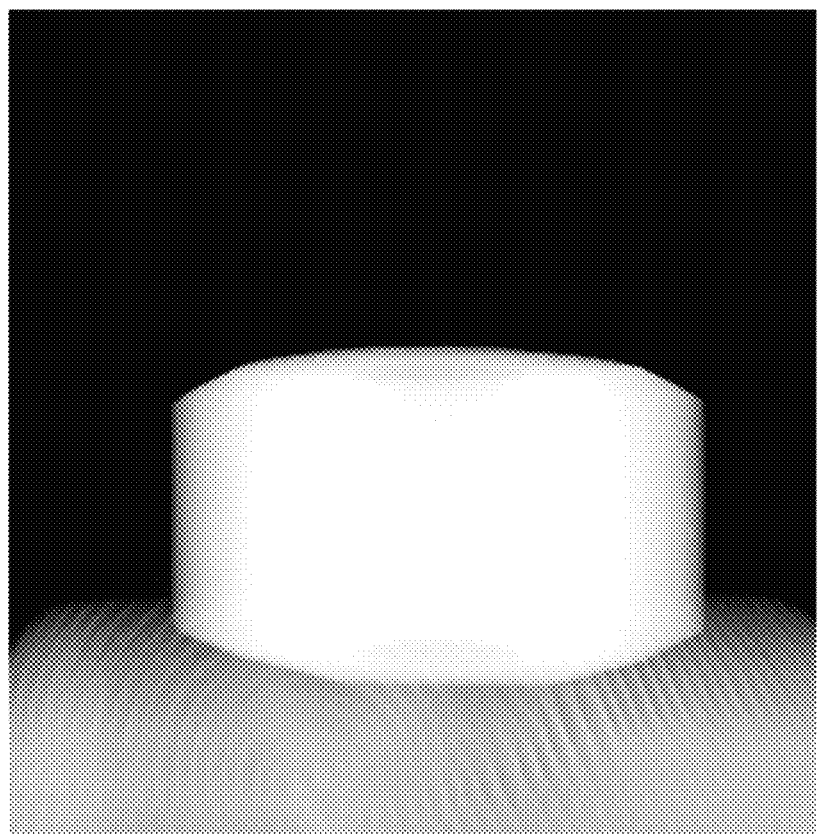
FIG. 3A is an individual x-ray shot illustrating a nut on top of wood, according to an embodiment of the present invention.

In order to test the technology, a specimen consisting of an aluminum nut placed on top of wood was used, and eight x-ray shots were taken from different angles. The source and detector positions and orientations were known. An individual shot 300 of the nut is shown in FIG. 3A.

Figure 3B:
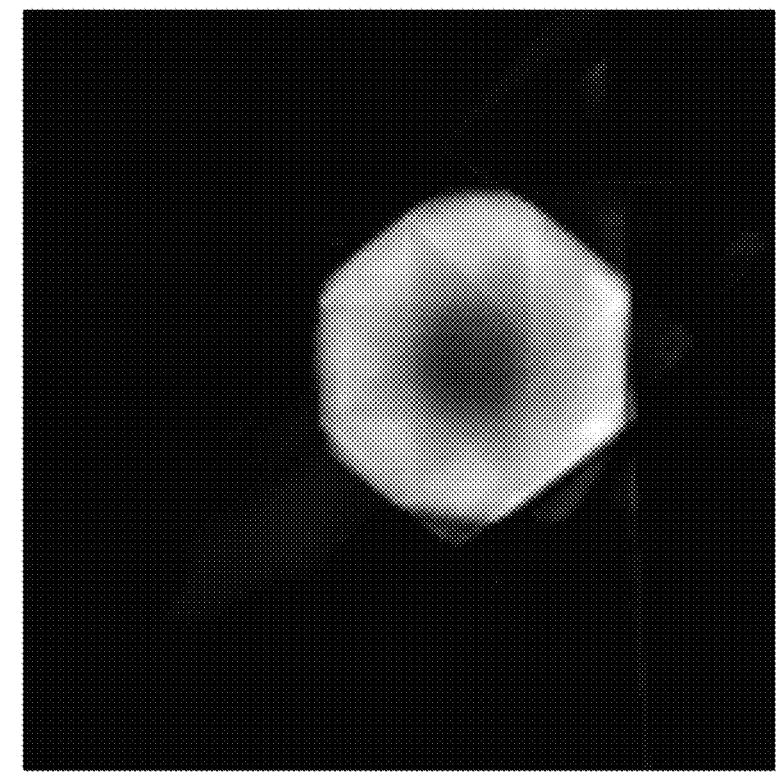
FIG. 3B is a slice of a volume image of the nut, according to an embodiment of the present invention.
Figure 3C:
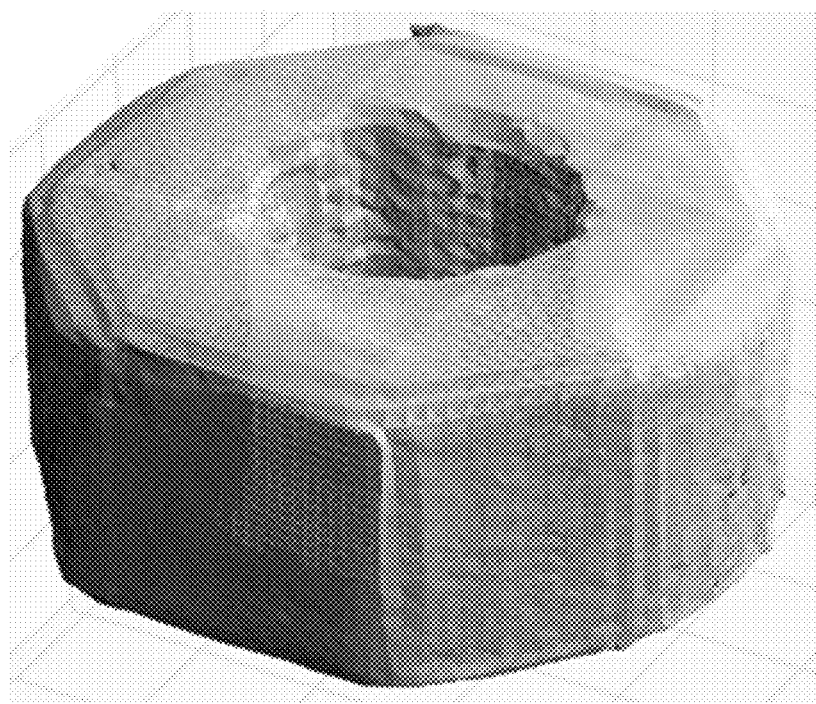
FIG. 3C is a three-dimensional isosurface volume image of the nut reconstructed using only eight x-ray shots, according to an embodiment of the present invention.

In order to perform reconstruction, the eight images were preprocessed, the relationships between the detector pixels and volume image voxels were determined, and volume was solved for using ART-based techniques. Preprocessing only took a few seconds using software that was heavily optimized for OpenCL and the treatment of large sparse matrices. A slice 310 of the volume image shown in FIG. 3B, and an isosurface volume image rendering 320 of the external surface is shown in FIG. 3C. While only eight shots were used here, conventional CT systems typically use thousands of x-ray shots to reconstruct a volume image.

Embodiments such as those illustrated in FIGS. 1 and 2 present a unique geometry that is not utilized by conventional x-ray systems. "Geometry," as used herein, refers to how the x-ray source and detector are geometrically placed to obtain x-ray information. The arbitrary measurement capabilities of some embodiments are novel. For instance, the x-ray source and detector can be placed at any suitable angle and/or range with respect to the region of interest (ROI—e.g., a target, a part of the target, a human or animal, a part of the human or animal, etc.). No ring geometry is enforced for this kind of measurement in some embodiments. This may be particularly beneficial for difficult to access ROIs on relatively large parts for which the x-ray source and detector are placed on opposite sides of some barrier. See FIG. 2. Advantages of some embodiments are listed in further detail below.

Portable: The x-ray source and detector may be lightweight and may be placed individually and independently around the ROI. In some embodiments, the source and detector may be mounted on tripods.

Positioning: The x-ray source and detector positions and orientations may be measured by one or more positioning systems. The positioning system(s) may include, but are not limited to, GPS, gyros, accelerometers, laser positioning systems, ultrasonic positioning systems, camera-based positioning systems, markers, string encoders, any combination thereof, or any other suitable location determination and positioning system. Such positioning information may also be back-calculated.

Sparse Measurement: Only a few x-ray shots are obtained for reconstruction purposes in some embodiments. The shots may be performed on an incomplete arc, with few different angles, etc.

Arbitrary Measurement: X-ray shots may be performed for any x-ray source and detector positions and are not constrained to a ring (i.e., the system is not dedicated to a specific ring geometry). This is in contrast to conventional systems that use a ring geometry in some fashion.

To perform x-ray CT, the algorithm should accommodate the geometry. The algorithm of some embodiments fundamentally uses ART. ART began in 1970 by using linear algebra techniques (first originating in the 1930s) to perform x-ray CT. Thus, ART has been used in some form for x-ray CT research for decades.

However, Radon transform-based x-ray CT remains the favorite of the industry and research since it has low computational complexity for high resolution three-dimensional (3D) images. Only recently has computing hardware become fast enough and sufficiently scaled to enable practical applications of ART in x-ray CT.

However, some embodiments, utilize advances in hardware technology and new algorithms in conjunction with ART. For instance, some embodiments use novel fast, accurate matrix formation for ART, voxel masking or recombination, and the refining of positions and orientations. A summary of some characteristics of the algorithm employed by some embodiments is provided below.

ART: Algebraic reconstruction techniques are used to perform x-ray CT.

3D Image: A high resolution volume image may be used for nondestructive evaluation (i.e., the target is not destroyed by the imaging process).

Fast and Accurate Matrix: The first step of the ART employed in some embodiments is to form a matrix relating the voxels to the detector pixels. This should be done quickly and accurately. The algorithm of some embodiments uses a modified ray tracing algorithm that uses a custom preprocessing step and data-parallel algorithms, resulting in high accuracy and superior computational performance as compared to conventional techniques. More specifically, conventional algorithms use rough approximations, which cause artifacts in the reconstructed 3D image.

Regularization: ART can simultaneously solve for multiple objectives, such as minimum error, minimum total variation (TV), etc., or force only valid solutions to exist through a process called regularization. Mathematically, "regularization" is the process of introducing additional information in order to solve an ill-posed problem or to prevent overfitting. One application of regularization could be noise removal in some embodiments. For instance, if it is known that the volume image should not be noisy, the solution can be regularized to minimize noise. As another example, if it is known that the volume image should always be positive, the solution can be regularized so only positive values exist. Regularization may be applied to any suitable known information without deviating from the scope of the invention.

Antialiasing: This a technique to smooth the appearance and increase the accuracy of voxel to detector pixel contributions. This technique is commonly used in custom shaders in video games.

Graphics Processing Unit (GPU): Use of one or more GPUs can provide processing for data-parallel algorithms.

Masking or Recombination: Detector pixels that are obviously not part of the ROI may be removed from the matrix or may be lumped together as one or more unknowns (e.g., a few unknowns) corresponding to the background or some value. This step significantly reduces matrix size, and hence, computation time.

Refine Positions and Orientation: In this portable technique, the exact position of the x-ray source and the exact position and orientation of the x-ray digital detector may not be known. Thus, they are treated as unknowns. The algorithm of some embodiments makes it possible to refine these unknowns to optimize a volume image metric. For example, the optimized metric could be image contrast, image sparsity, or total variation. This is in contrast to other optimization approaches in ART that only use the voxels as unknowns.

Fast and Accurate Matrix Formation

In some embodiments, the fast and accurate matrix formation is optimized for 2D digital detectors, cone beams, and GPU processing. It should be noted that it is typical in practice to make approximations in the matrix, and these approximations may make salt-and-pepper noise in the final 3D image reconstruction, which is destructive. However, some embodiments deploy a novel approach that has the same computational complexity as some of the best approximations known in the art, but no destructive approximations are made. Also, in some embodiments, the algorithm is light-weight and fast since 3D image reconstructions should be computed in the field for certain applications.

ART refers to a class of techniques that form the volume reconstruction problem into an algebraic system of equations in the form:

$$Av=d \qquad (1)$$

where uppercase bold letters indicate a matrix, lowercase bold letters indicate a vector, $d$ is the vectorized data corresponding to x-ray detector pixels, $v$ is the vectorized data corresponding to the volume image being reconstructed, and A is the matrix expressing the relationship from v to d.

Reconstruction aside, simply computing A can be a difficult task and is the focus of this section. Generally speaking, the matrix A has D (number of detector pixels) rows and V (number of voxels) columns, where italics denote a scalar number. Consequently, there are DV total elements in matrix A. Moreover, the number of detector pixels is, $$D = LWN \quad (2)$$

where L is the number of pixels along the detector length, W is the number of pixels along the detector width, and N is the number of detector locations and orientations around the ROI. In a typical instance, one may assume the following values for argument's sake: L=1000, W=1000, and N=100. This makes D=100,000,000 (i.e., $10^8$). Also, the number of voxels may be around this quantity, making V=$10^8$. Consequently, the matrix A may have $10^{16}$ elements, and it takes the same number of computations to compute the matrix.

In "big-O" notation, this computational complexity is O(DV), which is a way of expressing that the computation time is proportional to DV. In practice, it is common to store A as a sparse matrix since the vast majority of the $10^{16}$ elements are zero and do not contribute to matrix-vector operations. Thus, the storage complexity, as opposed to the computational complexity, is O($\rho$V), where $\rho$ is a scalar coefficient representing the average number of detector pixels influenced per voxel. In practice, O($\rho$V) is much smaller than O(DV), perhaps thousands or even millions of times smaller, depending on the size and number of x-ray shots collected and the desired number of volume image voxels.

A fast and accurate algorithm is desired to form the matrix A with a calculation complexity on the same order as the storage complexity without incurring unacceptable error from approximations. To this end, an algorithm was developed that employs the following steps: (1) compute indices of detector pixels influenced by each voxel; (2) transpose the indices to obtain voxel influence for each detector pixel; and (3) compute the values for the sparse matrix directly. This high-level view of the algorithm is useful for mathematically understanding the problem, but does not contain the particulars of software generation. More specifically, it does not contain details on computation, hardware acceleration, etc. The algorithm was specifically altered to be massively data-parallel and use local-worker memory to minimize global memory fetching so that it scales appropriately with graphics GPUs or co-processors. Consequently, the algorithm is described in more detail below.

```
for every shot (for-loop) {
    for every voxel (GPU-dispatch) {
        project voxel onto plane of the detector to determine pixel range
        in rows and columns and calculate number of influenced pixels;
    }
    for every voxel (for-loop) {
        compute row_ptr index for sparse matrix indexing of A^T;
    }
    for every voxel (GPU-dispatch) {
        compute col_ind using above row_ptr for sparse matrix indexing
        for A^T;
    }
    compute index transpose to find row_ptr and col_ptr for sparse
    matrix indexing of A from A^T;
    for every detector pixel (GPU-dispatch) {
        for every significant voxel (for-loop) {
            for every antialiased row (for-loop) {
                for every antialiased column (for-loop)* {
                    compute length of intersection of ray in voxel;
                }
            }
            average result and store entry in A;
        }
    }
    store A for shot;
}
end
```

It should be noted that sparse matrices are used exclusively in the algorithm, and the algorithm complexity is O($\rho$V). The nested for-loop that computes the length of intersection of the ray in each voxel is the most computationally expensive, and operates on the sparse matrix directly, thereby eliminating needless computation. The sparse matrix representation here is called compressed sparse row (CSR), which is a known, small, and computationally fast way to store a sparse matrix on a computer. As such, there is a row_ptr (array length D) storing the number of nonzero elements within the row and col_ind (array length O($\rho$V)) storing the column indices for every nonzero element in the matrix. Key optimization and algorithm design was made for steps labeled (GPU-dispatch) in this embodiment, which indicates that every step in the subsection is hardware accelerated on the GPU. Additionally, the step marked with an asterisk (*) denotes a place where the GPU compiler is able to unwrap an inner loop automatically for maximal performance. The result is a fast, accurate, and novel way to compute the sparse matrix A used for ART.

Voxel Masking or Recombination

Voxel masking or recombination is another important feature in some embodiments, which facilitates the reduction of matrix rows and columns by incorporating knowledge that some voxels are already known to contain no structure, or that some voxels are identical in value. The reduction of matrix size immediately reduces computation complexity without sacrificing 3D image quality. In some embodiments, x-ray shots may be subject to thresholding to identify significant pixels. Insignificant pixels may then be eliminated before reconstruction by eliminating rows of A and d in Eq. (1). Furthermore, insignificant pixels correspond to voxels that are already known (i.e., background). Known voxels can then be eliminated before reconstruction by eliminating columns of A and rows in v. In certain embodiments, a multi-resolution technique may be employed such that the reconstruction may be performed at first at low voxel density and subsequently at higher voxel densities. This multi-resolution technique may be important and non-trivial in some embodiments. Multi-resolution techniques may significantly reduce calculation complexity. Groups of voxels that do not change value between subsequent discretizations may be lumped, thusly, eliminating columns of A and rows in v.

Refining Positions and Orientation

Some embodiments refine x-ray source and x-ray detector positions and orientations since inaccuracies in the positions and orientations may corrupt the final 3D reconstruction by blurring or creating some other image artifacts. The refining process may include optimizing the positions and orientations with respect to an image metric including, but not limited to, image contrast, image sparsity, image detail, or any combination thereof. It should be noted that that conventional approaches do not perform this refining this since the dedicated geometry system employed does not require refining. Thus, conventional approaches only solve for the reconstructed 3D image. Additionally, this refining is performed with the previously described fast and accurate matrix formation since the matrix formation should be performed in every iteration of the position and orientation refining loop.

FIG. 4A is a flowchart illustrating a process for performing x-ray CT using ART-based techniques, according to an embodiment of the present invention. The process begins with receiving a plurality of x-ray shots from an x-ray detector and position information from at least one positioning system at 405. A fast, accurate matrix is then formed for each x-ray shot relating voxels to detector pixels via a modified ray tracing algorithm at 410 with antialiasing, which increases the accuracy of the voxel to detector pixel contributions. This matrix may eliminate the artifacts caused by conventional approaches that use rough approximations.

Masking or recombination is performed at 415 to remove detector pixels that are not part of the ROI or lump them together as one unknown. This step significantly reduces matrix size, and hence, computation time. Some steps of masking detector pixels may actually be performed before matrix formation to further reduce computation time (not shown). Once the final matrix is known, ART-based reconstruction is performed at 420 with regularization to produce a volume image. Finally, the output 3D volume image is rendered at 425 and output to a user for inspection. This embodiment may be particularly applicable if the positions and orientations of the x-ray source and detector are accurately known.

However, if the positions and orientations of the x-ray source and detector are not accurately known (e.g., due to lack of an accurate positioning system), they may be treated as unknowns and be iteratively refined to optimize a volume image metric. For example, the optimized metric could be image contrast, image sparsity, or total variation. Such a process is shown in flowchart 450 of FIG. 4B.

As with steps 405-420 of the process of FIG. 4A, a plurality of x-ray shots from an x-ray detector and position information are received from at least one positioning system at 455, a fast, accurate matrix is formed for each x-ray shot relating voxels to detector pixels via a modified ray tracing algorithm at 460 with antialiasing, masking or recombination is performed at 465 to remove detector pixels that are not part of the ROI or lump them together as one unknown, and ART-based reconstruction is performed at 470 with regularization to produce a volume image. However, in FIG. 4B, an iterative optimization process is performed. If the positions and orientations are not optimized at 475 due to not satisfying a volume image metric, the positions and orientations are refined at 480, and matrix formation and ART-based reconstruction are performed repeatedly in steps 460-470 until the positions and orientations satisfy the volume image metric and are optimized at 475. The 3D volume image is then rendered at 485 and output to a user for inspection.

Figure 5:
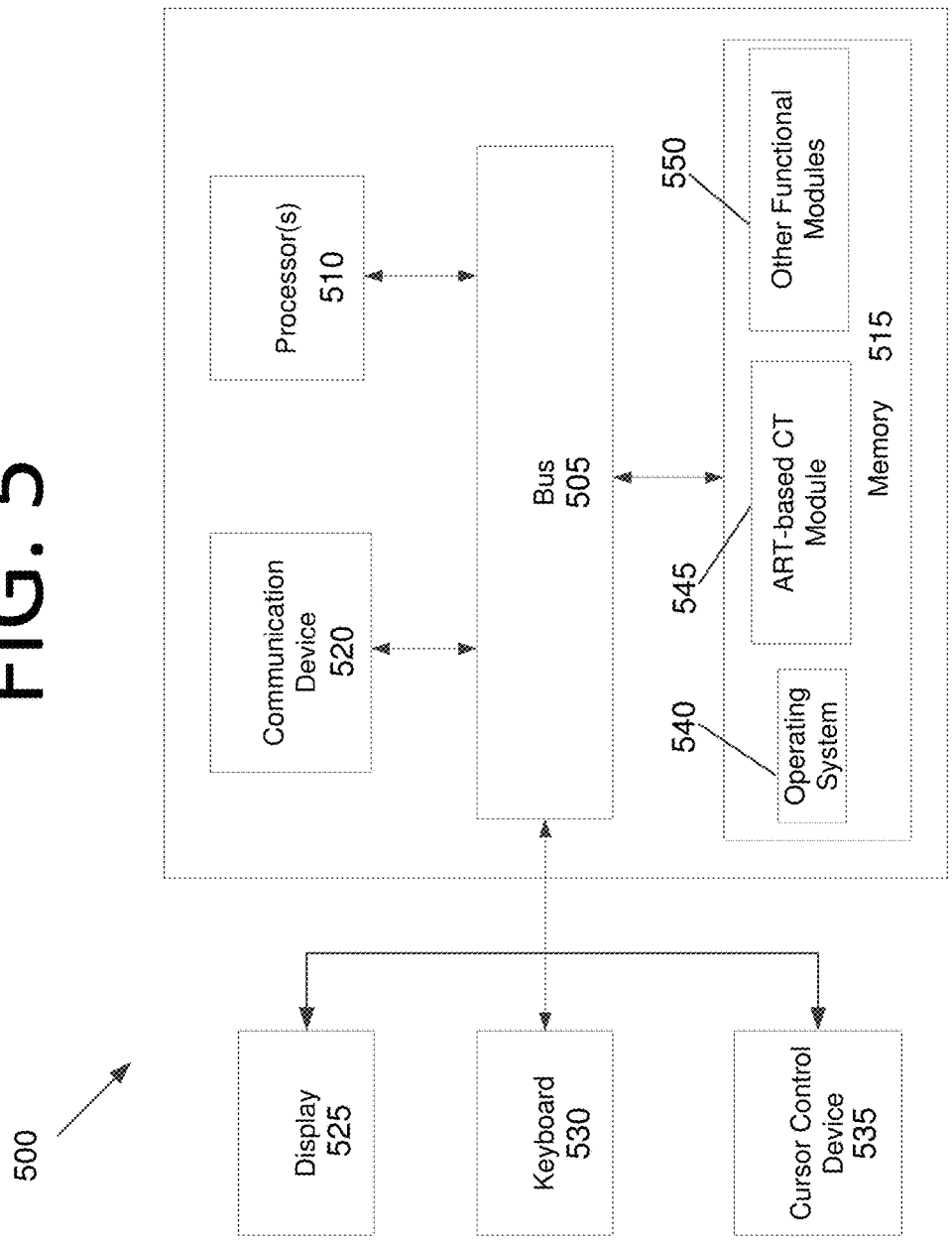
FIG. 5 is a block diagram illustrating a computing system configured to perform ART-based techniques to facilitate x-ray CT, according to an embodiment of the present invention.

FIG. 5 is a block diagram illustrating a computing system configured to perform ART-based techniques to facilitate x-ray CT, according to an embodiment of the present invention. Computing system 500 includes a bus 505 or other communication mechanism for communicating information, and processor(s) 510 coupled to bus 505 for processing information. Processor(s) 510 may be any type of general or specific purpose processor, including a central processing unit (CPU), a graphics processing unit (GPU), an application specific integrated circuit (ASIC), a field programmable gate array (FPGA), or any combination thereof. Processor(s) 510 may also have multiple processing cores, and at least some of the cores may be configured to perform specific functions. Multi-parallel processing may be used in some embodiments. Computing system 500 further includes a memory 515 for storing information and instructions to be executed by processor(s) 510. Memory 515 can be comprised of any combination of random access memory (RAM), read only memory (ROM), flash memory, cache, static storage such as a magnetic or optical disk, or any other types of non-transitory computer-readable media or combinations thereof. Additionally, computing system 500 includes a communication device 520, such as a transceiver and antenna, to wirelessly provide access to a communications network.

Non-transitory computer-readable media may be any available media that can be accessed by processor(s) 510 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 510 are further coupled via bus 505 to a display 525, such as a Liquid Crystal Display (LCD), for displaying information to a user. A keyboard 530 and a cursor control device 535, such as a computer mouse, are further coupled to bus 505 to enable a user to interface with computing system. However, in certain embodiments such as those for mobile computing implementations, a physical keyboard and mouse may not be present, and the user may interact with the device solely through display 525 and/or a touchpad (not shown). Any type and combination of input devices may be used as a matter of design choice.

Memory 515 stores software modules that provide functionality when executed by processor(s) 510. The modules include an operating system 540 for computing system 500. The modules further include an ART-based CT module 545 that is configured to facilitate ART-based CT by employing any of the approaches discussed herein or derivatives thereof. Computing system 500 may include one or more additional functional modules 550 that include additional functionality.

One skilled in the art will appreciate that a "system" could be embodied as an embedded computing system, a personal computer, a server, a console, a personal digital assistant (PDA), a cell phone, a tablet computing device, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The process steps performed in FIGS. 4A and 4B may be performed by a computer program, encoding instructions for the nonlinear adaptive processor to perform at least the processes described in FIGS. 4A and 4B, in accordance with embodiments of the present invention. The computer program may be embodied on a non-transitory computer-readable medium. The computer-readable medium may be, but is not limited to, a hard disk drive, a flash device, RAM, a tape, or any other such medium used to store data. The computer program may include encoded instructions for controlling the nonlinear adaptive processor to implement the processes described in FIGS. 4A and 4B, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the systems, apparatuses, methods, and computer programs of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A computer-implemented method, comprising:
receiving, by a computing system, a plurality of x-ray shots from an x-ray detector and position information from at least one positioning system, the plurality of x-ray shots comprising detector pixels;
forming a matrix, by the computing system, relating voxels to detector pixels for each of the plurality of x-ray shots, wherein the matrix is formed to reduce or eliminate volume image artifacts;
performing masking or recombination, by the computing system, to remove the detector pixels that are not part of a region of interest (ROI) or lump these detector pixels together as one or more unknowns;
performing algebraic reconstruction technique (ART)-based reconstruction with regularization, by the computing system, to produce a three-dimensional (3D) volume image; and
rendering and outputting the 3D volume image, by the computing system.

2. The computer-implemented method of claim 1, wherein when positions and orientations of an x-ray source and the x-ray detector are not known, the positions and orientations are treated as unknowns and the method further comprises:
iteratively refining and optimizing a volume image metric, by the computing system.

3. The computer-implemented method of claim 2, wherein the volume image metric comprises image contrast, image sparsity, or total variation.

4. The computer-implemented method of claim 1, wherein when positions and orientations of an x-ray source and the x-ray detector are not optimized due to not satisfying a volume image metric, the method further comprises:
   refining the positions and orientations, by the computing system; and
   performing the and matrix formation and ART-based reconstruction repeatedly until the positions and orientations satisfy the volume image metric and are optimized.

5. The computer-implemented method of claim 1, wherein
   the matrix expresses a relationship or transformation from a first vector to a second vector,
   the first vector comprises vectorized data corresponding to the 3D volume image being reconstructed, and
   the second vector comprises vectorized data corresponding to x-ray detector pixels.

6. The computer-implemented method of claim 5, wherein computing the matrix comprises computing indices of detector pixels influenced by each voxel, transposing the indices to obtain voxel influence for each detector pixel, and directly computing values for the matrix, which is sparse.

7. The computer-implemented method of claim 1, wherein the forming of the matrix for a given x-ray shot comprises:
   for each voxel, projecting the voxel onto a plane of the detector to determine pixel range in rows and columns; and
   calculating a number of influenced pixels.

8. The computer-implemented method of claim 7, wherein the forming of the matrix for the given shot further comprises:
   computing a row pointer index for sparse matrix indexing for a matrix transpose;
   computing a column index using the row pointer for sparse matrix indexing for the matrix transpose; and
   computing an index transpose to find a row pointer and column pointer for sparse matrix indexing for the matrix.

9. The computer-implemented method of claim 8, wherein the forming of the matrix for the given shot further comprises:
   for every significant voxel of every detector pixel in a given x-ray shot:
      for every antialiased column of every antialiased row, computing a length of intersection of a ray in the significant voxel; and
   averaging a result of the computing of the lengths of the intersections and storing the averaged result in the matrix.

10. The computer-implemented method of claim 1, wherein the matrix comprises a compressed sparse row (CSR) sparse matrix representation.

11. The computer-implemented method of claim 1, wherein the performing of the masking or recombination further comprises:
   reducing a number of rows and columns in the matrix by incorporating knowledge that some voxels are already known to contain no structure, that some voxels are identical in value, or both.

12. The computer-implemented method of claim 1, wherein the performing of the masking or recombination further comprises:
   subjecting each x-ray shot to thresholding to identify significant pixels; and
   eliminating remaining pixels by eliminating corresponding rows in the matrix and in a vector comprising vectorized data corresponding to the volume image being reconstructed.

13. The computer-implemented method of claim 1, wherein the lumping of the detector pixels together comprises lumping groups of voxels that do not change value between subsequent discretizations.

14. The computer-implemented method of claim 1, wherein fewer than 100 x-ray shots are used.

15. The computer-implemented method of claim 1, wherein when an accurate positioning system is not available and/or accurate positioning information is unavailable, the method further comprises:
   using a known target in the ROI as a reference; and
   based on the reference, applying an iterative solver to optimize a cost function representing a difference between an intermediate reconstructed 3D volume image and an ideal reference image.

16. A computer-implemented method, comprising:
   receiving, by a computing system, a plurality of x-ray shots from an x-ray detector and position information from at least one positioning system, the plurality of x-ray shots comprising detector pixels;
   forming a matrix, by the computing system, relating voxels to detector pixels for each of the plurality of x-ray shots to eliminate noise;
   performing masking or recombination, by the computing system, to remove the detector pixels that are not part of a region of interest (ROI) or lump these detector pixels together as one or more unknowns;
   performing algebraic reconstruction technique (ART)-based reconstruction with regularization, by the computing system, to produce a three-dimensional (3D) volume image; and
   rendering and outputting the 3D volume image, by the computing system.

17. The computer-implemented method of claim 16, wherein the performing of the masking or recombination further comprises:
   reducing a number of rows and columns in the matrix by incorporating knowledge that some voxels are already known to contain no structure, that some voxels are identical in value, or both.

18. The computer-implemented method of claim 16, wherein the performing of the masking or recombination further comprises:
   subjecting each x-ray shot to thresholding to identify significant detector pixels; and
   eliminating remaining detector pixels by eliminating corresponding rows in the matrix and in vectors comprising vectorized data corresponding to the detector pixels and the 3D volume image being reconstructed.

19. The computer-implemented method of claim 16, wherein the lumping of the detector pixels together comprises lumping groups of voxels that do not change value between subsequent discretizations.

20. The computer-implemented method of claim 16, wherein fewer than 100 x-ray shots are used.

* * * * *